Sept. 1, 1925. Re. 16,158

M. I. SCHAMBERG

PROJECTING LAMP

Original Filed Nov. 7, 1919 3 Sheets-Sheet 1

Inventor

M. I. Schamberg,

Witnesses:-

Chas. L. Gieseauer

Emory L. Groff

By D. P. Wolcan Jr.

Attorney

Sept. 1, 1925.
Re. 16,158
M. I. SCHAMBERG
PROJECTING LAMP
Original Filed Nov. 7, 1919 3 Sheets-Sheet 2
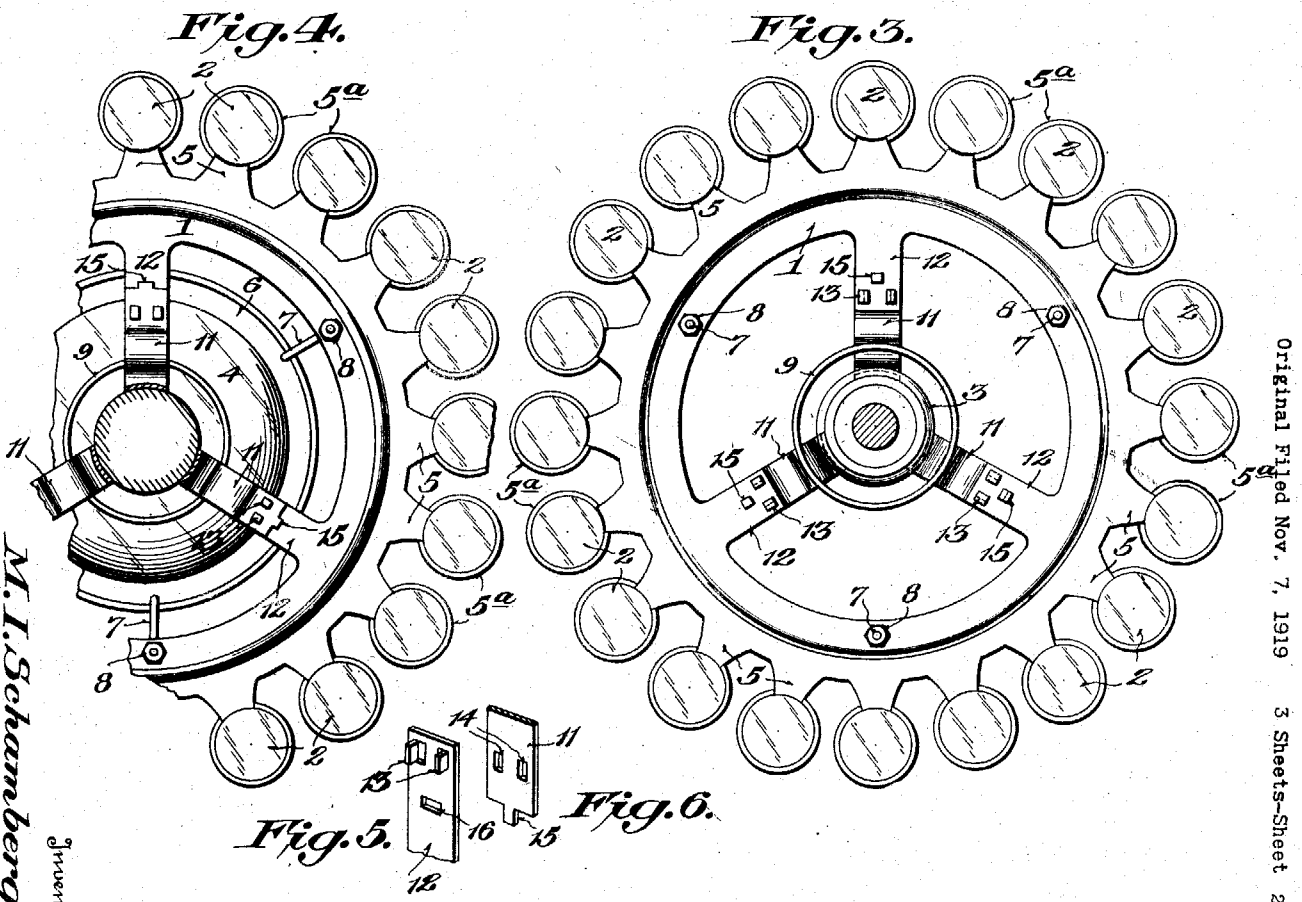
Inventor
M. I. Schamberg,
WITNESSES:-
Chas. L. Geistauer
Emory L. Groff
By S. P. Wickersham
Attorney Sept. 1, 1925. Re. 16,158

M. I. SCHAMBERG

PROJECTING LAMP

Original Filed Nov. 7, 1919 3 Sheets-Sheet 3

Inventor

M. I. Schamberg,

WITNESSES:-

Chas. R. Grieshauer

Emory L. Croff

By D. T. Worthington

Attorney

Reissued Sept. 1, 1925.

Re. 16,158

UNITED STATES PATENT OFFICE.

MORRIS I. SCHAMBERG, OF NEW YORK, N. Y.

PROJECTING LAMP.

Original No. 1,411,810, dated April 4, 1922, Serial No. 336,248, filed November 7, 1919. Application for reissue filed April 11, 1924. Serial No. 705,955.

*To all whom it may concern:*

Be it known that I, MORRIS I. SCHAMBERG, a citizen of the United States, and a resident of New York, county of New York, and State of New York, have invented new and useful Improvements in Projecting Lamps, of which the following is a specification.

My invention relates to improvements in means for concentrating and projecting light from a light source to a desired position, and is particularly useful for surgeons, dentists and others requiring a brilliant light in a limited field of operation. My invention comprises novel details of improvement and combinations of parts that will be more fully hereinafter set forth and then pointed out in the claims.

Reference is had to the accompanying drawings forming part hereof wherein

Fig. 3 is a face view partly in section on the line 3—3 in Fig. 2;

Fig. 4 is a fragmentary view taken substantially on the line 4—4 in Fig. 2;

Figs. 5 and 6 are detail views hereinafter referred to;

Similar numerals of reference indicate corresponding parts in the several views.

Figure 2:
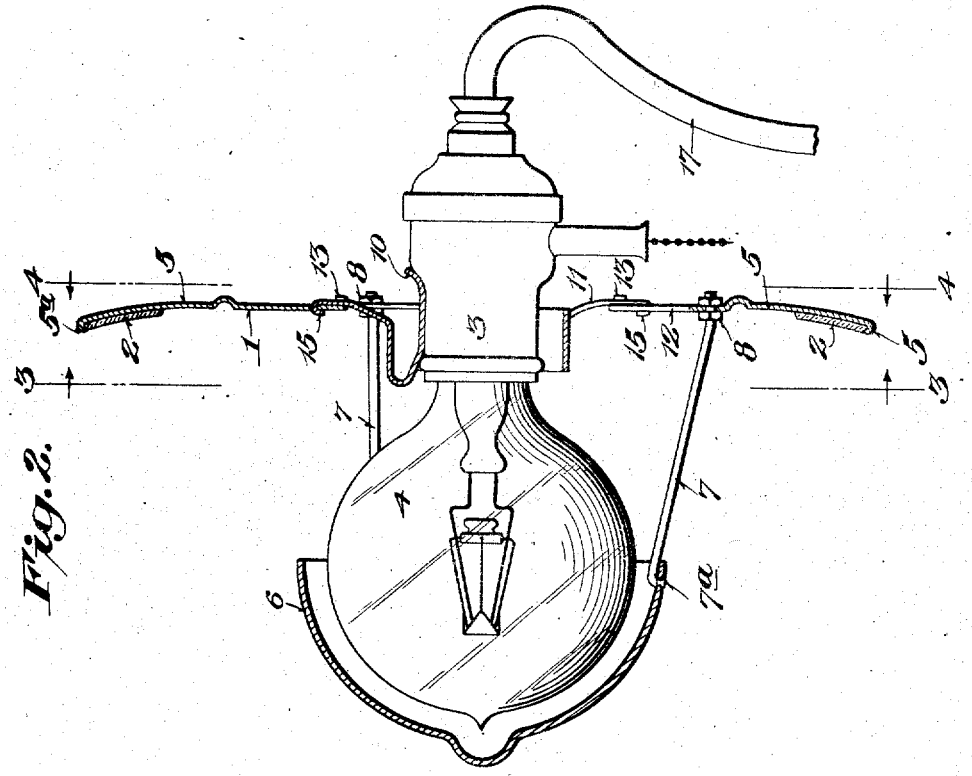
Fig. 2 is a section substantially on the line 2—2 in Fig. 1.

The numeral 1 indicates a frame shown in annular ring-like form adapted to support a plurality of annularly arranged reflectors 2 which are preferably concave mirror-like reflectors. To said frame a light source, such as an ordinary incandescent lamp socket 3, is adapted to be connected for supporting a suitable electric lamp 4 in such position that the rays of light from the said lamp will fall upon said annularly disposed reflectors to be projected therefrom in a desired direction. In the example illustrated in Figs. 1 to 4 the reflectors 2 are individually supported upon separate finger-like projections 5 suitably positioned and extending from the marginal portion of frame 1 in such a manner that the centers of the mirrors are equi-distant from the axis of said frame. Said frame and its projections may be made from a single piece of sheet metal stamped to desired shape, the marginal edges $5^a$ of the projections 5 being adapted to be folded to retain the corresponding reflector 2, as illustrated in Fig. 2. To prevent rays of light from lamp 4 being directly cast in a forward direction and to reflect or direct such rays to the reflectors 2, I provide a reflecting shield 6 located in front of lamp 4 the inner surface of said reflecting shield being polished or in mirror-like form to reflect rays therefrom brilliantly to the respective reflectors 2. Said shield 6 may be supported upon frame 1 in any suitable manner. As a simple and convenient means for supporting said shield I provide arms 7, which may be in the form of wires or rods, having their inner threaded ends extending through holes in said frame and receiving nuts 8 bearing against the opposite sides of frame 1, the outer ends of said arms being shown bent laterally at $7^a$ to engage holes $6^a$ in the marginal portion of shield 6. I have shown three of such arms attached to frame 1 although any desired number of said arms may be used.

The reflectors 2 are shown at a position back of light source 4 so as to receive rays not only directly from the light source but also indirectly by reflection from said source so that the reflector shield will not interfere with said direct rays. The arrangement permits all of said rays to converge to a focus point beyond said shield. The lamp socket 3 may be attached to frame 1 in any desired manner. As a simple and inexpensive means for such purpose I provide a ring-like member 9 shown disposed centrally within frame 1 and having spaced spring-like fingers 10 within said ring adapted to receive socket 3, whereby the latter may be conveniently pushed into and removed from said fingers. By the means described the frame 1 may support socket 3 in a central position therein. The ring-like member 9, as a convenient means of manufacture, may be attached to frame 1 by means of a desired number of projections 11 which may be formed with or secured to said ring and project outwardly for engagement with projections or arms 12 extending inwardly from frame 1. Said parts 11 and 12 may be secured in any desired manner. I have shown the part 12 having projections 13 entering apertures 14 in part 11 and the part 11 having a projection 15 entering the aperture 16 in part 12 (Figs. 5 and 6) whereby when said parts are assembled said projections may be folded to retain the parts together. The lamp may be supported in any desired manner as by the usual flexible conductor 17 or by means of any suitable frame or bracket, whereby light from the lamp may be projected upon the desired object.

Figure 1:
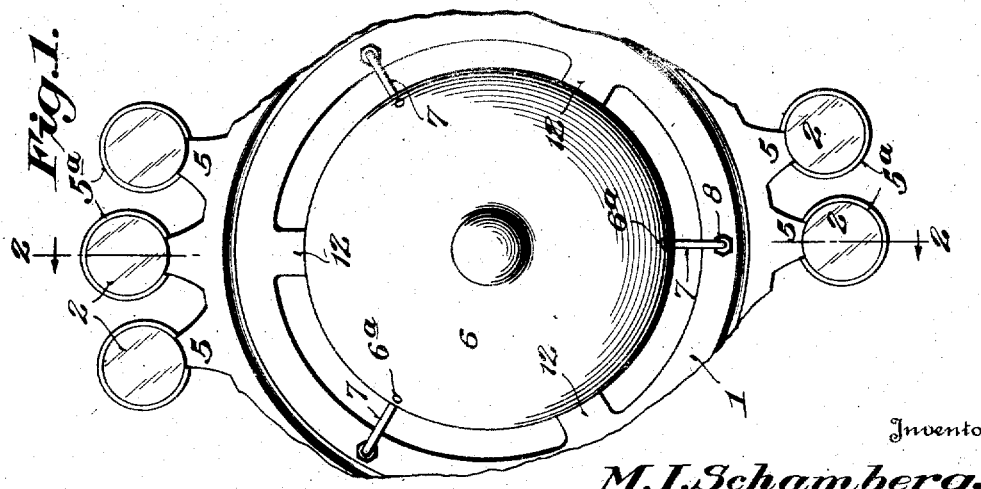
Figure 1 is a fragmentary front view of a projecting lamp embodying my invention.
Figure 8:
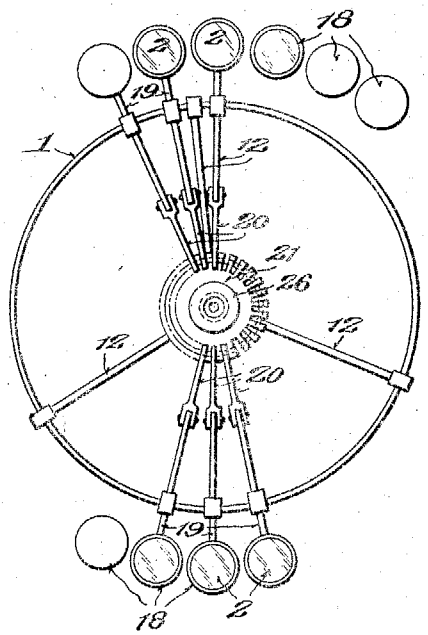
Fig. 8 is a fragmentary face view of Fig. 7.
Figure 7:
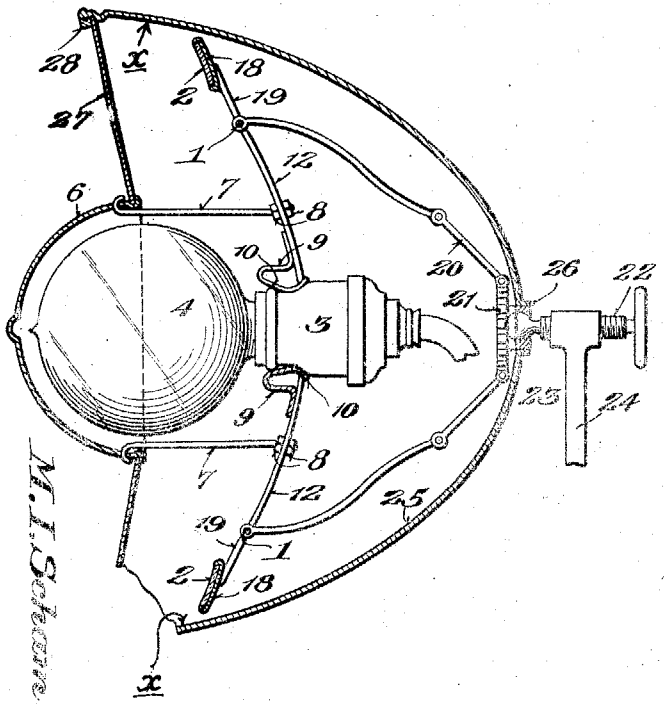
Fig. 7 is a central section illustrating my improvements comprising means to at will vary the direction of the projected rays of light.

While in Figs. 1 and 4 I have illustrated supporting arms 5 for the reflectors 2 as adapted to be bent as desired to cause the rays of light from said reflectors to be projected at the desired angle for concentrating rays from all of the reflectors upon an object, said reflectors may be supported for adjustment at will for casting rays therefrom as desired, means for which purpose are shown in Figs. 7 and 8. Each of the reflectors has a frame or backing 18 secured to projection or arm 19 pivotally supported upon frame 1, which frame in Figs. 7 and 8 is shown in the form of a ring-like wire. The arms 12 from said ring are provided with means to support socket 3, shown in the form of spring-fingers 10 secured to arms 12, whereby the socket for lamp 4 may be retained centrally disposed within the circle of reflectors 2. The arms 19 are shown pivotally connected by links 20 with a lamp member 21 that is adjustably supported. I have shown member 21 connected with threaded member 22 by universal joint 23, which threaded member operates in correspondingly threaded member 24 suitably supported, whereby when member 22 is rotated the member 21 will be moved in one or another direction and the arms 19 will be tilted and retained in said position for varying the position of the reflectors with respect to light source 4. I have shown the shield 6 supported by arms 7 and nuts 8 upon arms 12 in manner before described for retaining the shield in front of the lamp. The parts described with respect to Figs. 7 and 8 are also shown enclosed within a casing 25 in the nature of head lights for automobiles, the member 21 being supported in a bearing at 26 in said casing, which casing may be supported in any desired manner; but the rim portion $x$ thereof surrounds and projects forwardly of the individual reflectors thereby acting as a side shield for preventing lateral dispersion or glare of the light. The glass or lens 27 at the front of the casing 25 may be supported thereon in any desired or well known manner such as by ring 28. With the arrangement described the angle of the reflectors 2 with respect to the electric light 4 may be varied as desired so as to cause light projected from the lamp to be cast forwardly from the automobile at desired points toward or upon the road.

By means of my improvements the rays of light from the light source 4 will be projected directly upon the reflectors 2 as well as such rays reflected on said reflectors from the reflector shield 6 which rays will be consolidated and superimposed and will be projected to a desired position in accordance with the distance from the lamp of the object to be illuminated and with respect to the annular relation of the reflectors 2 to the light source 4. All of such rays converge to a focal point and by varying the angle of reflectors 2 with respect to the light source the area of light cast from said reflectors upon an object at a given distance may be increased or diminished as desired. The reflecting mirrors 2 may be of such character as to cause light rays from the source of light to be magnified and to magnify the whiteness of the light from the filament or arc of the light source whereby a brilliant light may be produced. By means of my invention the reflectors receive the light directly from the lamp filament in such a manner as to reflect such light forward upon a given space to increase the intensity of the light thereon. This result is effected by reason of the series of spaced concave reflectors located behind the light source and in position to project the rays forward around the light and its shield to a given position. The image of the lamp filament with its full light intensity is received by the reflectors and is projected therefrom forward to the focal point, a series of bright images of the intense light of the filament being outlined, and by using the light on an object at a predetermined distance from the light source superimposed rays from the reflectors give a brilliant and intense white light on the object without the glare that would be produced by the direct rays from the light source. By reason of the annular arrangement of the reflectors the light is projected forward upon an object to be illuminated in a manner to minimize shadows, as, for instance, if the hand or fingers of an operator be interposed in a portion of the light cast upon an object the remainder of the light will be so strong as to maintain a satisfactory illumination of the object.

My projecting lamp is particularly useful for projecting brilliant, strong light directly upon an object, such as in the mouth or other cavities of a patient, or upon desired parts of their bodies, for use of surgeons for their operations on patients and for dentists. My improvements, also, may be used in other relations, such as for reading lamps, for head lights, etc.

It will be understood that by means of my improvements a simple and relatively cheap and efficient projecting lamp is provided, since all of the reflectors 2 are arranged about a central light source receiving rays of light therefrom in an equal manner directly as well as receiving reflected rays from the reflecting shield 6, which is within all the light rays projected from the reflectors. Since the light rays are projected from the reflectors 2 angularly disposed regarding the light source, said rays may be concentrated within a certain area, and may be cast into the mouth of a patient without being cast into the patient's eyes, the shield 6 obstructing the direct rays from the light source into the patient's eyes.

My invention is not limited to the details of construction herein set forth, since the same may be varied, within the scope of the appended claims, without departing from the spirit of my invention.

A feature of particular importance in my invention is that the reflecting means is arranged substantially in the form of an annulus back of the light source without any reflecting medium within said annulus, whereby rays from the angularly disposed reflecting annulus may be concentrated on objects without direct parallel rays from the light source being reflected from within the annulus upon the same object. With the shield in front of the light source and no reflector behind the light source in a direct line from the object through the light source the advantage of preventing the rays from reaching the patient's eyes is attained.

Having thus described my invention, what I claim and desire to secure by Letters Patent is:

1. A shadow-reducing and glareless reflector unit for concentrating light rays, the said unit including a frame having means to support a light source and having means outside of said light source to support a plurality of annularly disposed circular reflectors, arms extending from said frame forwardly outside of said light source, and a reflecting shield carried by said arms in front of said light source to reflect rays therefrom to the first named reflectors.

2. A shadow-reducing and glareless reflector unit for concentrating light rays, the said unit including a frame having means to support a light source and having means to support a light source and to support a plurality of annularly disposed circular reflectors, a reflecting shield for the light source, and means to detachably connect said shield with said frame whereby the shield is supported in front of said light source to reflect rays therefrom to the first named reflectors.

3. A shadow-reducing and glareless reflector unit for concentrating light rays, the said unit including a ring-like frame having inwardly disposed projections and outwardly disposed arms, a ring having outwardly disposed projections attached to the first named projections, said ring having inner spaced spring-like fingers to receive a lamp socket, and reflectors secured to said arms to receive rays from a light source connected to said socket.

4. A shadow-reducing and glareless reflector unit for concentrating light rays, the said unit including an illuminating lamp, an opaque rearwardly-reflecting shield covering approximately the front hemisphere of the lamp and an annular series of individual circular concave reflecting mirrors arranged concentrically about and in rear of said opaque shield.

5. A shadow-reducing and glareless reflector unit for concentrating light rays, the said unit including the light element, an opaque rearwardly-reflecting shield covering the front portion of the light element, and a uniform annular series of circular individual reflecting mirrors arranged in rear of said shield and disposed at similar angles causing the light rays to converge and merge into a common focal area beyond said shield.

6. A shadow-reducing and glareless reflector unit for concentrating light rays, the said unit including an illuminating lamp, an opaque rearwardly-reflecting shield covering approximately the front hemisphere of the lamp, means for supporting said shield in a fixed position, and a uniform annular series of similar individual reflecting mirrors arranged in rear of said shield and in a circular plane beyond the rim thereof, said individual reflecting mirrors being disposed at similar angles to be exposed to the reflection from the shield and to the light from the uncovered hemisphere of the lamp and also arranged to cause the rays of light to converge and merge into a common focal area beyond the shield.

7. A shadow-reducing and glareless reflector unit for concentrating light rays, the said unit including a support for the illuminating lamp, an opaque rearwardly-reflecting shield covering approximately the front hemisphere of the lamp, and a uniform annular series of circular reflecting mirrors arranged in a circle in rear of and concentric with said shield and disposed at angles causing the light rays to converge and merge into a common focal area beyond the shield, and an opaque casing part or shield member disposed around and forwardly of said individual reflecting mirrors.

In testimony whereof I hereunto affix my signature.

MORRIS I. SCHAMBERG.